United States Patent
Lopaschuk

(10) Patent No.: US 6,653,090 B1
(45) Date of Patent: Nov. 25, 2003

(54) METHODS FOR MEASURING THE METABOLISM OF AND SCREENING FOR DRUGS IN ISOLATED HEARTS

(75) Inventor: Gary Lopaschuk, Alberta (CA)

(73) Assignee: University of Alberta, Edmonton (CA)

( * ) Notice: Subject to any disclaimer, the term of this patent is extended or adjusted under 35 U.S.C. 154(b) by 0 days.

(21) Appl. No.: 09/707,352

(22) Filed: Nov. 6, 2000

Related U.S. Application Data

(60) Provisional application No. 60/163,711, filed on Nov. 5, 1999.

(51) Int. Cl.$^7$ .................................................. C12Q 1/54
(52) U.S. Cl. ............................................. 435/14; 435/4
(58) Field of Search ........................................ 435/4, 14

(56) References Cited

U.S. PATENT DOCUMENTS 5,549,974 A * 8/1996 Holmes

OTHER PUBLICATIONS

Barr et al. (J. Pharm. Tox. Meth.) 38; 11–7; 1997.*
Liu et al. (Circ. Res. 1996; 79:940–8)*
Saddik et al. (J. Biol. Chem. vol. 266, No. 138 8162–70) 1991.*
Schonekess et al. (Circ. Res. 81: 540–9, 1997.*
Saddik et al., J. Biol. Chem. 266(13): 8162–81702 (1991).*
Saddik et al., J. Biol. Chem. 267(6); 3825–3831 (1992).*
de Groot et al. Biochim. Biophys. Acta 1006: 111–115 (1989).*
Fraser et al., Am. J. Physiol. 275: H1533–H1541 (1998).*
Schonekess et al., Circ. Res 81: 540–549 (1997).*
Barr et al., J. Pharm. Tox. Methods 38: 11–17 (1997).*
Lopaschuk et al., Mol. Cell Biochem. 172: 137–147 (1997).*

* cited by examiner

*Primary Examiner*—Jean C. Witz
(74) *Attorney, Agent, or Firm*—John R. Wetherell, Jr.

(57) ABSTRACT

The invention provides novel methods for measuring the metabolism of the heart. The invention also provides methods for screening for compounds that can effect the metabolism of the heart under normal and abnormal, such as stressed, e.g., ischemic, conditions. An isolated heart is used in these methods. These screening methods can be used to identify therapeutic drugs.

51 Claims, No Drawings

METHODS FOR MEASURING THE METABOLISM OF AND SCREENING FOR DRUGS IN ISOLATED HEARTS

RELATED APPLICATIONS

This application claims the benefit of priority under 35 U.S.C. §119(e) of U.S. Provisional Application No. 60/163, 711, filed Nov. 5, 1999. The aforementioned application is explicitly incorporated herein by reference in entirety and for all purposes.

TECHNICAL FIELD

This invention relates to medicine and physiology. In particular, the invention provides methods for measuring the metabolism of the heart. The invention also provides methods for screening for compounds that can effect the metabolism of the heart under normal and abnormal, such as stressed, e.g., ischemic, conditions. These screening methods can be used to identify therapeutic drugs.

BACKGROUND

Glycogen is an important source of glucose for energy substrate metabolism and ATP generation in the heart. The contribution of glycogen as an endogenous source of glucose depends on both energy substrate availability as well as the metabolic status of the heart. The regulation of glycogen synthesis and degradation (turnover) has been extensively studied in the liver. Although the heart has a great potential for the synthesis and storage of glycogen, myocardial glycogen turnover is less well understood, particularly under ischemic or reperfused conditions.

When cardiac muscle is adequately perfused, exogenous glucose is transported into myocytes, where it primarily either enters the glycolytic pathway or is stored as glycogen. This glycogen can also be subsequently mobilized to provide a source of endogenous glucose for glycolysis. During ischemia, when the supply of $O_2$ and exogenous substrates is impaired, fatty acid and glucose oxidation are inhibited and ATP generation from anaerobic glycolysis increases. Although glycolysis produces ATP in the absence of $O_2$, excessive rates of glycolysis may be deleterious during and after severe ischemia due to the production of protons from the hydrolysis of glycolytically derived ATP. During reperfusion of ischemic hearts, glycolytic rates continue to exceed glucose oxidation rates. This uncoupling of glycolysis from glucose oxidation continues to be an important source of protons and leads to intracellular acidosis, $Na^+$ accumulation, and $Ca^{2+}$ overload. Glucose released from glycogen under conditions of glycogenolysis may be preferentially oxidized. If so, then endogenous glucose may be contributing less to proton production than exogenous glucose. Thus, the preferential utilization of endogenous glucose, rather than exogenous glucose, may result in lower rates of proton production and $Ca^{2+}$ overload.

However, the relationships between various parameters of metabolism, including endogenous and exogenous glucose metabolism, proton production, fatty acid utilization and the like, are not completely understood.

Current methods of detecting energy metabolism rely on indirect approaches and thus have significant drawbacks. These include: (1) they only indirectly assess energy metabolism in the heart; (2) they cannot quantitatively determine flux through the individual energy producing pathways; (3) they cannot directly assess either the contribution of glucose from glycogen or fatty acid from triacyiglycerol as a source of energy; (4) they cannot measure energy metabolism in the presence of physiological workloads or in the presence of myocardial ischemia, and (5) they cannot directly compare energy metabolism to oxygen consumption in the heart.

SUMMARY

The invention provides novel methods for measuring overall endogenous and exogenous fatty acid utilization and glucose metabolism, complete energy metabolism and exogenous energy metabolism by a working heart under "normal" and ischemic conditions. Using these novel methods, the invention provides methods for screening for compounds that can effect the metabolism of the heart under normal and abnormal, such as stressed, e.g., ischemic, conditions. These screening methods can be used to identify therapeutic drugs.

The invention provides methods for measuring overall endogenous and exogenous fatty acid utilization by a working heart comprising the following steps: (a) providing an isolated working heart; (b) measuring fatty acid oxidation and lactate oxidation in the working heart simultaneously; and, (c) measuring triacyiglycerol turnover in the working heart, wherein step (c) can be performed during or after step (b), thereby measuring overall endogenous and exogenous fatty acid utilization in the working heart.

In this method, as in all methods of the invention, the heart can be derived from any source; in one embodiment, the isolated working heart is a mammalian heart, such as a monkey or ape heart, a rat heart, a rabbit heart, or a mouse heart, The heart can be isolated by any methodology. In this and all methods of the invention the isolated working heart can be subjected to a trauma or a drug before a measurement or sample is taken; for example, the trauma can be an induced ischemia. Alternatively, the ischemia can be induced during or after initiation of any of the measurements. The measuring can be done or the sample taken before, during and/or after the ischemic event. In one embodiment, the isolated working heart is reperfused before measuring or sampling. The reperfusion can be designed to induce and/or prolong a state of ischemia. The reperfusion can be designed to allow slow or fast recovery from an ischemic event.

In one embodiment, the isolated working heart is reperfused to induce a low-flow ischemia. The ischemia can be induced by stopping perfusate flow through a left atrial inflow line and limiting flow throughout an aortic outflow line, thereby generating any range of aortic perfusion rates and any degree of ischemia. Severe ischemia can be induced by generating aortic perfusion rates ranging from about 0.5 ml/min to about 2 ml/min. Moderate ischemia can be induced by generating aortic perfusion rates from about 2 ml/min to about 5 ml/min. Mild ischemia can be induced by generating aortic perfusion rates from about 5 ml/min to about 15 ml/min.

In the methods of the invention, fatty acid oxidation can be measured by any known methodology or protocol. In one exemplary embodiment, fatty acid oxidation of the isolated heart is measured by quantitative collection of $^{14}CO_2$ from [$^{14}C$]palmitate, as described, e.g., by Saddik (1991) J. Biol. Chem. 266:8162–8170; Saddik (1992) J. Biol. Chem. 267:3825–3831; Lopaschuk (1997) Mol. Cell. Biochem. 172:137–147; or, Barr (1997) J. Pharmacol. Methods 38:11–17; or, combinations thereof or variations thereof.

In another exemplary embodiment, fatty acid oxidation of the isolated heart is measured by quantitative collection of $^3H_2O$ production from [$^3H$]palmitate, as described, e.g., by Saddik (1991) supra; Saddik (1992) supra; or, Lopaschuk (1997) supra; or, Barr (1997) supra; or, combinations thereof or variations thereof.

In the methods of the invention, lactate oxidation can be measured by any known methodology or protocol; for example, it can be measured by quantitative collection of $^{14}CO_2$ from [$^{14}C$]lactate, as described, e.g., by Liu (1996) Circ. Res. 79:940–948; or, Lopaschuk (1997) supra; or, Barr (1997) supra; or combinations thereof or variations thereof.

In another exemplary embodiment, lactate oxidation is measured by quantitative collection of $^{14}CO_2$ from [$^{14}C$] lactate, while simultaneously measuring palmitate oxidation, as described by Liu (1996) supra, or variations thereof.

In the methods of the invention, triacylglycerol turnover can be measured by any known methodology or protocol; for example, it can be measured using a pulse-chase procedure in which quantitative collection of $^3H_2O$ production from exogenous [$^3H$]palmitate and quantitative collection of $^{14}CO_2$ from endogenous [$^{14}C$]palmitate labeled triacylglycerol is measured simultaneously, as described, e.g., by Saddik (1991) supra, Saddik (1992) supra; or variations thereof.

In another exemplary embodiment, triacylglycerol turnover is measured by quantitative collection of $^{14}CO_2$ from exogenous [$^{14}C$]palmitate, and quantitative collection of $^3H_2O$ production from endogenous [$^3H$]palmitate labeled triacylglycerol, as described, e.g., by Saddik (1991) supra; Saddik (1992) supra; or variations thereof.

The invention also provides a method for measuring overall endogenous and exogenous glucose metabolism in a working heart comprising the following steps: (a) providing an isolated working heart; (b) measuring glycolysis and glucose oxidation in the working heart, wherein the glycolysis and glucose oxidation are measured simultaneously or serially; and, (c) measuring glycogen turnover in the working heart, wherein step (c) can be performed during or after step (b), thereby measuring overall endogenous and exogenous glucose metabolism in the working heart. As with all methods of the invention, the isolated working heart can be derived from any source; for example, the heart can be a mammalian heart, such as rat heart, a rabbit heart or a mouse heart. As with all methods of the invention, the isolated working heart is subjected to a trauma or a drug before the measurement is taken. Alternatively, the trauma or a drug can be induced during or after initiation of any of the measurements. The trauma can be an ischemia. The isolated working heart can be reperfused before, during and/or after inducement of the ischemia.

In the methods of the invention, glycolysis can be measured by any known methodology or protocol; for example, it can be measured by quantitative collection of $^3H_2O$ production from [$^3H$]glucose, as described, e.g., by Saddik (1991) supra; Saddik (1992) supra; Lopaschuk (1997) supra; or, Barr (1997) supra; or combinations or variations thereof.

In an alternative embodiment, glycolysis is measured by quantitative collection of $^3H_2O$ production from [$^3H$] glucose, while simultaneously measuring glucose or lactate oxidation, as described, e.g., by Liu (1996) supra, or variations thereof.

In the methods of the invention, glucose oxidation can be measured by any known methodology or protocol; for example, it can be measured by quantitative collection of $^{14}CO_2$ from [$^{14}C$]glucose, as described, e.g., by Liu (1996) supra, or variations thereof.

In an alternative embodiment, glucose oxidation is measured by quantitative collection of $^{14}CO_2$ from [$^{14}C$]glucose, while simultaneously measuring palmitate oxidation, as described, e.g., by Liu (1996) or variations thereof.

In the methods of the invention, glycogen turnover can be measured by any known methodology or protocol; for example, it can be measured by simultaneous quantitative collection of $^{14}CO_3$ from exogenous [$^{14}C$]glucose and $^3H_2O$ from endogenous glycogen labeled with [$^3H$]glucose, as described, e.g., by Schonekess (1997) Circ. Res. 81:540–549; or variations thereof.

In an alternative embodiment, glycogen turnover is measured by simultaneous quantitative collection of $^3H_2O$ from exogenous [$^3H$]glucose and $^{14}CO_2$ from endogenous glycogen labeled with [$^{14}C$]glucose, as described e.g., by Schonekess (1997) supra; or variations thereof.

The invention provides a method for measuring complete energy metabolism in a working heart comprising the following steps: (a) providing an isolated working heart; (b) measuring fatty acid oxidation and lactate oxidation in the working simultaneously; and (c) measuring glycolysis, glucose oxidation, triacylglycerol turnover and glycogen turnover in the working heart, wherein the glycolysis, glucose oxidation, triacyiglycerol turnover and glycogen turnover are measured simultaneously or serially, wherein step (c) can be performed during or after step (b), thereby measuring complete energy metabolism in the working heart.

As with all methods of the invention, the heart can be derived from any source; in one embodiment, the isolated working heart is a mammalian heart, such as a monkey or ape heart, a rat heart, a rabbit heart, or a mouse heart. The heart can be isolated by any methodology. In this and all methods of the invention the isolated working heart can be subjected to a trauma or a drug before a measurement or sample is taken; for example, the trauma can be an induced ischemia. Alternatively, the trauma or a drug can be induced during or after initiation of any of the measurements. The measuring can be done or the sample taken before, during and/or after the ischemic event. In one embodiment, the isolated working heart is reperfused before measuring or sampling. The reperfusion can be designed to induce and/or prolong a state of ischemia. In one embodiment, the reperfusion can be designed to allow slow or fast recovery from an ischemic event.

The invention provides a method for measuring exogenous energy metabolism during ischemia by a working heart comprising the following steps: (a) providing an isolated ischemic working heart, wherein the ischemia is induced by perfusion at a severe low-flow; (b) measuring fatty acid oxidation and lactate oxidation in the ischemic working heart simultaneously; and, (c) measuring glycolysis and glucose oxidation in the ischemic working heart, wherein the glycolysis and glucose oxidation are measured simultaneously or serially, wherein step (c) can be performed during or after step (b), thereby measuring exogenous energy metabolism in the working heart during ischemia. In one embodiment, the isolated working heart is perfused at a low flow rate. The low flow can be generated by a method comprising stopping perfusate flow through the left atrial inflow line and aortic outflow line.

The low flow (and resulting ischemia) can be generated by a method comprising stopping perfusate flow through the left atrial inflow line and limiting flow throughout aortic outflow line. Thus, different degrees, or severities, of ischemia can be produced by modulating aortic perfusion rates. Severe ischemia can be induced when aortic flows range from about 0.5 ml/min to about 2 ml/min. Moderate ischemia can be induced by inducing aortic perfusion rates from about 2 ml/min to about 5 ml/min. Mild ischemia can be induced by inducing aortic perfusion rates from about 5 ml/min to about 15 ml/min.

The invention provides a method for measuring overall energy metabolism in an ischemic working heart comprising the following steps: (a) providing an isolated ischemic working heart, wherein the ischemia is induced by perfusion at a low flow rate; (b) measuring fatty acid oxidation and lactate oxidation in the ischemic working heart simultaneously; and, (c) measuring glycolysis, glucose oxidation, triacylglycerol turnover and glycogen turnover in the ischemic working heart, wherein the glycolysis, glucose oxidation, triacylglycerol turnover and glycogen are measured simultaneously or serially, wherein step (c) can be performed during or after step (b), thereby measuring overall energy metabolism in the ischemic working heart.

The invention provides a method for measuring overall energy metabolism during reperfusion an ischemic working heart comprising the following steps: (a) providing an isolated reperfused working heart, wherein the reperfusion begins after ischemia is induced in the heart; (b) measuring fatty acid oxidation and lactate oxidation in the reperfused working heart simultaneously; followed by (c) measuring glycolysis, glucose oxidation, triacylglycerol turnover and glycogen turnover in the reperfused working heart, wherein the glycolysis, glucose oxidation, triacylglycerol turnover and glycogen are measured simultaneously, or, serially, thereby measuring overall energy metabolism during reperfusion of the ischemic working heart.

The invention provides a method for screening for compounds capable of modulating the energy metabolism of a working heart comprising the following steps: (a) providing an isolated heart; (b) providing a test compound; (c) measuring the overall fatty acid utilization of the heart using any protocol, including those as forth herein, the overall measure of glucose metabolism of the heart using any protocol, including those as forth herein, the complete energy metabolism of the heart using any protocol, including those as forth herein; the exogenous energy metabolism of the heart using any protocol, including those as forth herein, the overall energy metabolism of the heart during ischemia using any protocol, including those as forth herein, or, the overall energy metabolism during reperfusion of the working heart after inducement of ischemia using any protocol, including those as forth herein; (d) contacting the test compo to the heart; and, (e) measuring the change in overall fatty acid utilization of the heart using any protocol, including those as forth herein, the overall measure of glucose metabolism of the heart using any protocol, including those as forth herein, the complete energy metabolism of the heart using any protocol, including those as forth herein, the exogenous energy metabolism of the heart using any protocol, including those as forth herein, the overall energy metabolism of the heart during ischemia using any protocol, including those as forth herein, or, the overall energy metabolism during reperfusion of the working heart after inducement of ischemia using any protocol, including those as forth herein, wherein a change in the overall fatty acid utilization, the overall measure of glucose metabolism, the complete energy metabolism, the exogenous energy metabolism, the overall energy metabolism of the heart during ischemia, or, the overall energy metabolism during reperfusion of the working heart after inducement of ischemia, after addition of the test compound indicates that the test compound can modulate the energy metabolism of a working heart.

The invention provides a method for screening for compounds capable of modulating the energy metabolism of a working heart comprising the following steps: (a) providing an isolated working heart; (b) contacting the isolated working heart with a test compound; (c) measuring the overall fatty acid utilization of the heart using any protocol, including those as forth herein, the overall measure of glucose metabolism of the heart using any protocol, including those as forth herein, the complete energy metabolism of the heart using any protocol, including those as forth herein, the exogenous energy metabolism of the heart using any protocol, including those as forth herein, the overall energy metabolism of the heart during ischemia using any protocol, including those as forth herein, or, the overall energy metabolism during reperfusion of the working heart after inducement of ischemia using any protocol, including those as forth herein; (d) contacting the isolated working heart without or with more or less of the test compound; and (e) measuring the change in overall fatty acid utilization of the heart using any protocol, including those as forth herein, the overall measure of glucose metabolism of the heart using any protocol, including those as forth herein, the complete energy metabolism of the heart using any protocol, including those as forth herein, the exogenous energy metabolism of the heart using any protocol, including those as forth herein, the overall energy metabolism of the heart during ischemia using any—protocol, including those as forth herein, or, the overall energy metabolism during reperfusion of the working heart after inducement of ischemia using any protocol, including those as forth herein, wherein a change in the overall fatty acid utilization, the overall measure of glucose metabolism, the complete energy metabolism, the exogenous energy metabolism, the overall energy metabolism of the heart during ischemia, or, the overall energy metabolism during reperfusion of the working heart after inducement of ischemia, after withdrawal or dilution or increase in amount of the test compound indicates that the test compound can modulate the energy metabolism of a working heart. As with all the methods of the invention, the isolated working heart can be a mammalian heart, e.g., a rat heart, a rabbit heart or a mouse heart.

In one embodiment, the test compound is administered to the heart by perfusion. As with all methods of the invention, the isolated working heart can be perfused/reperfused at a controlled low rate to induce a desired amount of ischemia.

All publications, patents, patent applications, GenBank sequences and ATCC deposits, cited herein are hereby expressly incorporated by reference for all purposes.

The details of one or more embodiments of the invention are set forth in the accompanying drawings and the description below. Other features, objects, and advantages of the invention will be apparent from the description and drawings, and from the claims.

DETAILED DESCRIPTION

The invention provides novel methods for measuring the metabolism of the heart, including methods for measuring overall endogenous and exogenous fatty acid utilization and glucose metabolism, complete energy metabolism and exogenous energy metabolism by a working heart under "normal" and ischemic conditions.

The invention also provides methods for screening for compounds that can effect the metabolism of the heart under normal and abnormal, such as stressed, e.g., ischemic, conditions. These screening methods can be used to identify therapeutic drugs.

The invention provides a number of methods that allow for the determination of overall energy metabolism in the heart. They include: (1) methodologies to simultaneously measure glycolysis and glucose oxidation in the heart; (2) methodologies to directly measure triacyiglycerol turnover in the heart; (3) methodologies to directly measure glycogen turnover in the heart.

Two important determinants of energy metabolism in the heart are the work performed by the heart and the type of energy substrates to which the heart is exposed. The heart also contains sizeable endogenous pools of glycogen and triacylglycerol that can provide glucose and fatty acids, respectively, as a source of fuel for the heart. The experimental systems previously developed and used have not been able to control for these variables. An advantage of one aspect of the invention is that the isolated working heart system allows for the measurement of overall energy metabolism in hearts perfused at physiologically relevant workloads or during induced stress (e.g., at desired levels of ischemia) and in the presence of physiologically relevant energy substrates. The invention provides novel methods for measuring overall endogenous and exogenous fatty acid utilization by a working heart; for measuring overall endogenous and exogenous glucose metabolism in a working heart; for measuring complete energy metabolism in a working heart; for measuring exogenous energy metabolism during ischemia by a working heart; for measuring overall energy metabolism in an ischemic working heart; for measuring overall energy metabolism during reperfusion an ischemic working heart; for screening for compounds capable of modulating the energy metabolism of a working heart; for screening for compounds capable of modulating the energy metabolism of a working heart, that include measurements of glycolysis, glucose oxidation, lactate oxidation, fatty acid oxidation and the contribution of triacylglycerol fatty acids and glycogen glucose to energy production. The methods of the invention provide an ability to measure various aspects of metabolism, and overall metabolism and energy utilization, during exposure to drugs and/or trauma, such as ischemia, e.g., induced severe, moderate or light myocardial ischemia. Myocardial ischemia is a very prevalent clinical problem in society and alterations in energy metabolism are important contributing factors in cell injury and death during and following myocardial ischemia.

Other aspects of the invention provide approaches for determining the effects of compounds that have efficacy in the treatment of ischemic heart disease. The invention can be used to identify novel compounds that modify energy metabolism and performance of a working heart under various conditions, including during exposure to drugs and/or trauma, such as ischemia, e.g., induced severe, moderate or light myocardial ischemia. The invention can also be used in the preparation and analysis of new compounds that are able to optimize energy metabolism in myocardial cells and in the intact heart and optimize heart performance under various conditions. Use of the invention will result in new classes of drugs for the treatment and prevention of various heart conditions and diseases; for example, the screening methods of the invention will lead to the introduction of new drugs that lessen the severity of ischemic heart disease by optimizing energy metabolism in the heart.

In contrast to current methods of detecting energy metabolism in the heart, which rely on indirect approaches, the invention provides novel methods that can directly assess energy metabolism in the heart; can quantitatively determine flux through the individual energy producing pathways; can directly assess either the contribution of glucose from glycogen or fatty acid from triacyiglycerol as a source of energy; can measure energy metabolism in the presence of physiological workloads, or, in the presence of myocardial ischemia; and, (5) can directly compare energy metabolism to oxygen consumption in the heart. For example, in one aspect of the invention, an isolated heart is contacted with a compound either randomly selected from a library (e.g., a combinatorial library) or one suspected of having heart metabolism modulating ability. The effect of the compound on the heart is then determined. In one embodiment, the effect of the compound on heart energy, heart metabolism or heart metabolite production, or heart performance, is compared to a control or a standard heart measurement.

Definitions

Unless defined otherwise, all technical and scientific terms used herein have the meaning commonly understood by a person skilled in the art to which this invention belongs.

Measuring Fatty Acid Oxidation

The invention provides methods for measuring overall endogenous and exogenous fatty acid utilization in the working heart, exogenous energy metabolism during ischemia, and, complete energy metabolism by a working heart, comprising measuring fatty acid oxidation and lactate oxidation in the working heart simultaneously. The invention also provides a method for screening for compounds capable of modulating the energy metabolism of a working heart comprising measuring fatty acid oxidation.

In one exemplary embodiment, the fatty acid oxidation is measured by quantitative collection of $^{14}CO_2$ from [$^4C$] palmitate, as described, e.g., by Saddik (1991) J. Biol. Chem. 266:8162; or Lopaschuk (1997) Mol. Cell. Biochem. 172:137–147; or Barr (1997) J. Pharmacol. Methods 38:11–17; or, combinations thereof or variations thereof.

In another exemplary embodiment, fatty acid oxidation of the isolated heart is measured by quantitative collection of $^3H_2O$ production from [$^3H$]palmitate, as described, e.g., by Saddik (1991) supra; or, Lopaschuk (1997) supra; or, Barr (1997) supra; or, combinations thereof or variations thereof.

Measuring Lactate Oxidation

The invention provides methods for measuring overall endogenous and exogenous fatty acid utilization in the working heart, exogenous energy metabolism during ischemia, for measuring overall energy metabolism in an ischemic working heart, and, complete energy metabolism by a working heart, comprising measuring fatty acid oxidation and lactate oxidation in the working heart simultaneously. The invention also provides methods for screening for compounds capable of modulating the energy metabolism of a working heart comprising measuring lactate oxidation.

In the methods of the invention, lactate oxidation can be measured by quantitative collection of $^{14}CO_2$ from [$^{14}C$] lactate, as described, e.g., by Liu (1996) Circ. Res. 79:940–948; or, Lopaschuk (1997)supra; or Barr (1997) supra; or, combinations thereof or variations thereof.

In another exemplary embodiment, lactate oxidation is measured by quantitative collection of $^{14}CO_2$ from [$^{14}C$] lactate, while simultaneously measuring palmitate oxidation, as described by Liu (1996) supra.

Measuring Triacylglycerol Turnover

The invention provides methods for measuring overall endogenous and exogenous fatty acid utilization and for measuring complete energy metabolism by a working heart, for measuring overall energy metabolism during reperfusion an ischemic working heart, and, for measuring overall energy metabolism in an ischemic working heart, comprising measuring triacylglycerol turnover. The invention also provides methods for screening for compounds capable of modulating the energy metabolism of a working heart comprising measuring triacylglycerol turnover.

In the methods of the invention, triacyiglycerol turnover can be measured using a pulse-chase procedure in which quantitative collection of $^3H_2O$ production from exogenous [$^3H$]palmitate and quantitative collection of $^{14}CO_2$ from endogenous [$^{14}C$]palmitate labeled triacyiglycerol is measured simultaneously, as described, e.g., by Saddik (1991) supra.

In another exemplary embodiment, triacylglycerol turnover is measured by quantitative collection of $^{14}CO_2$ from exogenous [$^4C$]palmitate, and quantitative collection of $^3H_2O$ production from endogenous [$^3H$]palmitate labeled triacylglycerol, as described, e.g., by Saddik (1991) supra.

Measurement of Glycolysis

The invention provides methods for measuring overall endogenous and exogenous glucose metabolism and complete energy metabolism by a working heart, for measuring exogenous and overall energy metabolism during reperfusion an ischemic working heart, and, for measuring overall energy metabolism in an ischemic working heart, comprising measuring glycolysis. The invention also provides methods for screening for compounds capable of modulating the energy metabolism of a working heart comprising measuring glycolysis.

In the methods of the invention, glycolysis can be measured by any known methodology or protocol; for example, it can be measured by quantitative collection of $^3H_2O$ production from [$^3H$]glucose, as described by Saddik (1991); supra; or, Lopaschuk (1997) supra; or, Barr (1997) supra; or, combinations or variations thereof.

Measuring Glucose Oxidation

The invention provides methods for measuring overall endogenous and exogenous glucose metabolism and complete energy metabolism by a working heart, for measuring exogenous and overall energy metabolism during reperfusion an ischemic working heart, and, for measuring overall energy metabolism in an ischemic working heart, comprising measuring glucose oxidation. The invention also provides methods for screening for compounds capable of modulating the energy metabolism of a working heart comprising measuring glucose oxidation.

In the methods of the invention, glucose oxidation can be measured by any known methodology or protocol; for example, it can be measured by quantitative collection of $^{14}CO_2$ from [$^{14}C$]glucose, as described, e.g., by Liu (1996) supra, or variations thereof.

In an alternative embodiment, glucose oxidation is measured by quantitative collection of $^{14}CO_2$ from exogenous [$^{14}C$]glucose, while simultaneously measuring palmitate oxidation, as described, e.g., by Liu (1996) or variations thereof.

Measuring Glycogen Turnover

The invention provides methods for measuring overall endogenous and exogenous glucose metabolism and complete energy metabolism by a working heart, for measuring overall energy metabolism during reperfusion an ischemic working heart, and, for measuring overall energy metabolism in an ischemic working heart, comprising measuring glycogen turnover. The invention also provides methods for screening for compounds capable of modulating the energy metabolism of a working heart comprising measuring glycogen turnover.

In the methods of the invention, glycogen turnover can be measured by any known methodology or protocol; for example, it can be measured by simultaneous quantitative collection of $^{14}CO_2$ from exogenous [$^{14}C$]glucose and $^3H_2O$ from endogenous glycogen labeled with [$^3H$]glucose, as described, e.g., by Schonekess (1997) Circ. Res. 8 1:540–549; or variations thereof.

In an alternative embodiment, glycogen turnover is measured by simultaneous quantitative collection of $^3H_2O$ from exogenous [$^3H$]glucose and $^{14}CO_2$ from endogenous glycogen labeled with [$^{14}C$]as described e.g., by Schonekess (1997) supra; or variations thereof.

Glycogen turnover can be assessed by measuring the simultaneous rates (in $\mu$mol glucose min$^{-1}$ g dry wt$^{-1}$) of glycogen synthesis ($G_{in}$) and degradation ($G_{out}$) that occur during each phase of the perfusion protocol. Apparent rates ($G'_{in}$ and $G'_{out}$) can be calculated from the difference in glycogen content measured at the beginning and end of each phase of the perfusion protocol. This calculation can be performed for unlabeled glycogen as well as for the component of glycogen that became labeled with either [$^3H$]glucose or [$^{14}C$]glucose.

The rates $G_{in}$ and $G_{out}$, averaged for each phase of perfusion can be calculated by incorporating values for the changes in unlabeled and labeled glycogen during each phase of perfusion. During the 60-mm period of aerobic perfusion, the rate of change ($dG_{net}/dt$) of total glycogen (labeled and unlabeled) between time 0 ($G_0$) and the end of the 60-min period of aerobic perfusion ($G_{60}$) is equal to the difference between $G_{in}$ and $G_{out}$ and can be calculated as follows $$dG_{net}/dt = [G_{60} - G_0 60] = G_{in} - G_{out} \tag{1}$$

Similarly, the rate of change ($dG_{hot}/dt$) of labeled glycogen between time 0 ($G_{hot,0}$) and the end of aerobic perfusion ($G_{hot,60}$) is equal to the difference between glycogen synthesis ($G_{in}$) and the rate of degradation of the labeled component of the glycogen pool. The rate of degradation varies according to the proportion of glycogen that is labeled; this proportion is 0% at time 0 and is determined experimentally at time 60. Consequently, the rate of synthesis at time 0 ($dG_{hot,0}/dt$), just before the addition of labeled glucose, is equal to $G_{in}$, whereas the rate of synthesis at time 60 ($G_{hot,60}/dt$) is equal to $G_{in} - [G_{out} (G_{hot}/G_{60})]$. Thus the average rate of incorporation of radiolabeled glucose into glycogen ($G_{hot,avg}/dt$) may be calculated from the experimentally determined incorporation of radiolabeled glucose $G_{hot}/60$ as well as from the average of the rates of incorporation at time 0 ($dG_{hot,0}/dt$) and at time 60 ($G_{hot,60}/dt$). The equation is as follows $$G_{hot}/60 = [dG_{hot,0}/dt + G_{hot,60}/dt]/2$$
$$= \{2G_{in} - [G_{out} (G_{hot}/G_{60})]\}/2 \tag{2}$$

Values for average rates G and G can be calculated from Eqs. 1 and 2. With the use of a similar approach, average rates G and G can be calculated for the periods of low-flow ischemia and reperfusion.

Heart Isolation and Perfusions

The invention provides methods and compositions for measuring overall endogenous and exogenous fatty acid utilization and glucose metabolism, complete energy metabolism and exogenous energy metabolism by a working heart under "normal" and ischemic conditions. The methods comprise use of isolated hearts from laboratory animals. Animals are housed and treated according to accepted standards of care, e.g., as those set by the Canadian Council of Animal Care.

Hearts can be isolated from any animal, including mice, rats, rabbits, monkeys and the like. Male Sprague-Dawley rats are typically used as experimental models.

Animals are anesthetized, e.g., with pentobarbital sodium (60 mg/kg ip). After induction of anesthesia, hearts are rapidly removed and placed in ice-cold buffer, e.g., Krebs-Henseleit solution. The hearts are then cannulated, e.g., as described by Finegan (1996) Am. J. Physiol. 271 (Heart Circ. Physiol. 40): H2116–H2125; and, perfused via the aorta. Perfusion is typically done during a 10 minute equilibration period.

In one exemplary protocol, hearts are then switched to working mode and perfused at 37° C. under aerobic conditions at a constant left atrial preload (11.5 mmHg) and aortic afterload (80 mmHg). Perfusate can consist of a modified Krebs-Henseleit solution containing 1.2 mM palmitate prebound to 3% BSA, 2.5 mM $Ca^{2+}$ 100 µU/ml insulin, and 11 mM glucose and was oxygenated with carbogen (95% $CO_2$–5% $O_2$).

If a low-flow ischemia protocol is desired, hearts are perfused under aerobic conditions for 60 min and then subjected to low-flow ischemia (0.5 ml/min) for 60 min, followed by 30 mm of reperfusion. Reperfusion is initiated by the removal of the clamps on the preload and afterload lines. This allowed flow into the left atrium at a rate that is influenced by the ability of each heart to eject fluid into the aortic afterload line. If afterload pressure is not maintained artificially during reperfusion, the ability of each heart to eject perfusate can be determined. Hearts are paced at about 300 beats/min throughout each phase of the perfusion protocol (voltage adjusted as necessary) with the exception of the initial 5 min of reperfusion, during which hearts are allowed to beat spontaneously. At the end of the perfusion protocol, hearts are rapidly frozen with the use of Wollenberger clamps cooled to the temperature of liquid $N_2$. Additional groups of hearts also can be frozen at the start of the aerobic perfusion period (time 0) and immediately before or after the period of low-flow ischemia. Frozen tissues are pulverized and the resulting powders stored at −80° C.

Screening of Compounds

The invention provides a method for screening for compounds capable of modulating the energy metabolism of a working heart. The test compounds can be administered by perfusion or direct administration onto or into the heart tissue.

The test compounds can be based on compositions known to effect metabolism, heart performance, cell physiology, and the like, or, the test compound can be derived from a library, containing a large number of potential therapeutic compounds or "candidate compounds." Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. Preparation and screening of combinatorial chemical libraries are well known to those of skill in the art, see, e.g., U.S. Pat. Nos. 6,096,496; 6,075,166; 6,054,047; 6,004,617; 5,985,356; 5,980,839 5,917,185; 5,767,238. Such combinatorial chemical libraries include, but are not limited to, peptide libraries (see, e.g., U.S. Pat. No. 5,010,175; Furka (1991) Int. J. Pept. Prot. Res., 37: 487–493, Houghton et al. (1991) Nature, 354: 84–88). Other chemistries for generating chemical diversity libraries include, but are not limited to: peptoids (see, e.g., WO 91/19735), encoded peptides (see, e.g., WO 93/20242), random bio-oligomers (see, e.g., WO 92/00091), benzodiazepines (see, e.g., U.S. Pat. No. 5,288,514), diversomers such as hydantoins, benzodiazepines and dipeptides (see, e.g., Hobbs (1993) Proc. Nat. Acad. Sci. USA 90: 6909–6913), vinylogous polypeptides (see, e.g., Hagihara (1992) J. Amer. Chem. Soc. 114: 6568), nonpeptidal peptidomimetics (see, e.g., Hirschmann (1992) J. Amer. Chem. Soc. 114: 9217–9218), analogous organic syntheses of small compound libraries (see, e.g., Chen (1994) J. Amer. Chem. Soc. 116: 2661), oligocarbamates (see, e.g., Cho (1993) Science 261:1303), and/or peptidyl phosphonates (see, e.g., Campbell (1994) J. Org. Chem. 59: 658); for carbohydrate libraries, see, e.g., Liang et al. (1996) Science 274: 1520–1 522, U.S. Pat. No. 5,593,853; for small organic molecule libraries, see, e.g., for isoprenoids U.S. Pat. 5,569,588; for thiazolidinones and metathiazanones, U.S. Pat. No. 5,549, 974; for pyrrolidines, U.S. Pat. Nos. 5,525,735 and 5,519, 134; for morpholino compounds, U.S. Pat. No. 5,506,337; for benzodiazepines U.S. Pat. No. 5,288,514.

EXAMPLES

The following examples are offered to illustrate, but not to limit the claimed invention.

Example 1

Protocols for Measuring the Metabolism of Isolated Hearts

Protocols used in the methods of the inventions are found in Saddik and Lopaschuk (1991) J. Biol. Chem. 266:8162–8170; Lopaschuk and Barr (1997) Mol. Cell. Biochem. 172:137–147; Barr (1997) J. Pharmacol. Methods 38:11–17; Liu et al. (1996) Circ. Res. 79:940–948; Saddik and Lopaschuk (1991) J. Biol. Chem. 267:3825–3831; and Schönekess et al. (1997) Circ. Res. 81:540–549, the entire contents of each of which is hereby expressly incorporated by reference. These papers specifically describe protocols for measuring fatty acid oxidation, lactate oxidation, glycolysis, glucose oxidation, triglycerol turnover and glycogen turnover. They also describe methods for isolating hearts, perfusing hearts, and generating a state of ischemia in an isolated heart.

A number of embodiments of the invention have been described. Nevertheless, it will be understood that various modifications may be made without departing from the spirit and scope of the invention. Accordingly, other embodiments are within the scope of the following claims.

What is claimed is:

1. A method for measuring overall endogenous and exogenous fatty acid utilization by a working heart comprising the following steps (a) providing an isolated working heart;

(b) measuring fatty acid oxidation and lactate oxidation in the working heart simultaneously; and (c) measuring triacylglycerol turnover in the working heart, wherein step (c) can be performed during or after step (b), thereby measuring overall endogenous and exogenous fatty acid utilization in the working heart.

2. The method of claim 1, wherein the isolated working heart is a mammalian heart.

3. The method of claim 2, wherein the isolated working heart is a rabbit heart, a rat heart or a mouse heart.

4. The method of claim 1, wherein the isolated working heart is subjected to a trauma or a drug.

5. The method of claim 4, wherein the trauma is ischemia.

6. The method of claim 1, wherein the isolated working heart is reperfused.

7. The method of claim 6, wherein the isolated working heart is reperfused at a low flow rate to induce ischemia.

8. The method of claim 7, wherein the ischemia is induced by stopping perfusate flow through a left atrial inflow line and limiting flow throughout an aortic outflow line, thereby generating any range of aortic perfusion rates and any degree of ischemia.

9. The method of claim 7, wherein severe ischemia is induced by generating aortic perfusion rates ranging from about 0.5 ml/min to about 2 ml/min.

10. The method of claim 7, wherein moderate ischemia is induced by generating aortic perfusion rates from about 2 ml/min to about 5 ml/min.

11. The method of claim 7, wherein mild ischemia is induced by generating aortic perfusion rates from about 5 ml/min to about 15 ml/min.

12. The method of claim 1, wherein fatty acid oxidation is measured by quantitative collection of $^{14}CO_2$ from palmitate.

13. The method of claim 1, wherein fatty acid oxidation is measured by quantitative collection of $^3H_2O$ production from palmitate.

14. The method of claim 1, wherein lactate oxidation is measured by quantitative collection of $^{14}CO_2$ from lactate.

15. The method of claim 1, wherein lactate oxidation is measured by quantitative collection of $^{14}CO_2$ from lactate, while simultaneously measuring palmitate oxidation.

16. The method of claim 1, wherein triacylglycerol turnover is measured by using a pulse-chase procedure in which quantitative collection of $^3H_2O$ production from exogenous palmitate and quantitative collection of $^{14}CO_2$ from endogenous palmitate labeled triacylglycerol is measured simultaneously.

17. The method of claim 1, wherein triacylglycerol turnover is measured by quantitative collection of $^{14}CO_2$ from exogenous palmitate and quantitative collection of $^3H_2O$ production from endogenous palmitate labeled triacylglycerol.

18. A method for measuring overall endogenous and exogenous glucose metabolism in a working heart comprising the following steps
(a) providing an isolated working heart;
(b) measuring glycolysis and glucose oxidation in the working heart, wherein the glycolysis and glucose oxidation are measured simultaneously, or, serially; and,
(c) measuring glycogen turnover in the working heart, wherein step (c) can be performed during or after step (b), thereby measuring overall endogenous and exogenous glucose metabolism in the working heart.

19. The method of claim 18, wherein the isolated working heart is a mammalian heart.

20. The method of claim 19, wherein the isolated working heart is a rabbit heart, a rat heart or a mouse heart.

21. The method of claim 18, wherein the isolated working heart is subjected to a trauma or a drug.

22. The method of claim 21, wherein the trauma is ischemia.

23. The method of claim 18, wherein the isolated working heart is reperfused.

24. The method of claim 18, wherein glycolysis is measured by quantitative collection of $^3H_2O$ production from glucose.

25. The method of claim 18, wherein glycolysis is measured by quantitative collection of $^3H_2O$ production from glucose, while simultaneously measuring glucose or lactate oxidation.

26. The method of claim 18, wherein glucose oxidation is measured by quantitative collection of $^{14}CO_2$ from glucose.

27. The method of claim 18, wherein glucose oxidation is measured by quantitative collection of $^{14}CO_2$ from glucose, while simultaneously measuring palmitate oxidation.

28. The method of claim 18, wherein glycogen turnover is measured by simultaneous quantitative collection of $^{14}CO_2$ from exogenous glucose and $^3H_2O$ from endogenous glycogen labeled with glucose.

29. The method of claim 18, wherein glycogen turnover is measured by simultaneous quantitative collection of $^3H_2O$ from exogenous glucose and $^{14}CO_2$ from endogenous glycogen labeled with glucose.

30. A method for measuring complete energy metabolism in a working heart comprising the following steps
(a) providing an isolated working heart;
(b) measuring fatty acid oxidation and lactate oxidation in the working heart simultaneously; and
(c) measuring glycolysis, glucose oxidation, triacylglycerol turnover and glycogen turnover in the working heart, wherein the glycolysis, glucose oxidation, triacylglycerol turnover and glycogen turnover are measured simultaneously, or, serially, wherein step (c) can be performed during (b), thereby measuring complete energy metabolism in the working heart.

31. The method of claim 30, wherein the isolated working heart is a mammalian heart.

32. The method of claim 31, wherein the isolated working heart is a rabbit heart, a rat heart or a mouse heart.

33. The method of claim 30, wherein the isolated working heart is subjected to a trauma or a drug.

34. The method of claim 33, wherein the trauma is ischemia.

35. The method of claim 30, wherein the isolated working heart is reperfused.

36. A method for measuring exogenous energy metabolism during ischemia by a working heart comprising the following steps
(a) providing an isolated ischemic working heart, wherein the ischemia is induced by perfusion at a low flow rate;
(b) measuring fatty acid oxidation and lactate oxidation in the ischemic working heart simultaneously; and,
(c) measuring glycolysis and glucose oxidation in the ischemic working heart, wherein the glycolysis and glucose oxidation are measured simultaneously, or, serially, wherein step (c) can be performed during or after step (b), thereby measuring exogenous energy metabolism in the working heart during ischemia.

37. The method of claim 36, wherein the isolated working heart is a rabbit heart, a rat heart or a mouse heart.

38. The method of claim 36, wherein the ischemia is induced by stopping perfusate flow through a left atrial inflow line and limiting flow throughout an aortic outflow line, thereby generating any range of aortic perfusion rates and any degree of ischemia.

39. The method of claim 36, wherein severe ischemia is induced by generating aortic perfusion rates ranging from about 0.5 ml/min to about 2 ml/min.

40. The method of claim 36, wherein moderate ischemia is induced by generating aortic perfusion rates from about 2 ml/min to about 5 ml/min.

41. The method of claim 36, wherein mild ischemia is induced by generating aortic perfusion rates from about 5 ml/min to about 15 ml/min.

42. A method for measuring overall energy metabolism in an ischemic working heart comprising the following steps
   (a) providing an isolated ischemic working heart, wherein the ischemia is induced by perfusion at a low flow rate;
   (b) measuring fatty acid oxidation and lactate oxidation in the ischemic working heart simultaneously; and
   (c) measuring glycolysis, glucose oxidation, triacylglycerol turnover and glycogen turnover in the ischemic working heart, wherein the glycolysis, glucose oxidation, triacylglycerol turnover and glycogen are measured simultaneously, or, serially, wherein step (c) can be performed during step (b), thereby measuring overall energy metabolism in the ischemic working heart.

43. A method for measuring overall energy metabolism during reperfusion in an ischemic working heart comprising the following steps
   (a) providing an isolated reperfused working heart, wherein the reperfusion begins after ischemia is induced in the heart;
   (b) measuring fatty acid oxidation and lactate oxidation in the reperfused working heart simultaneously; followed by
   (c) measuring glycolysis, glucose oxidation, triacylglycerol turnover and glycogen turnover in the reperfused working heart, wherein the glycolysis, glucose oxidation, triacylglycerol turnover and glycogen are measured simultaneously thereby measuring overall energy metabolism during reperfusion of the ischemic working heart.

44. A method for screening for compounds capable of modulating the energy metabolism of a working heart comprising the following steps
   (a) providing an isolated heart;
   (b) providing a test compound;
   (c) measuring the overall fatty acid endogenous and exogenous utilization of the heart as set forth in claim 1, the overall measure of glucose metabolism of the heart as set forth in claim 18, the complete energy metabolism of the heart as set forth in claim 30, the exogenous energy metabolism of the heart as set forth in claim 36, the overall energy metabolism of the heart during ischemia as set forth in claim 42, or, the overall energy metabolism during reperfusion of the working heart after inducement of ischemia as set forth in claim 43;
   (d) contacting the test compound to the heart; and
   (e) measuring the change in overall endogenous and exogenous fatty acid utilization of the heart as set forth in claim 1, the overall measure of glucose metabolism of the heart as set forth in claim 18, the complete energy metabolism of the heart as set forth in claim 30, the exogenous energy metabolism of the heart as set forth in claim 36, the overall energy metabolism of the heart during ischemia as set forth in claim 42, or, the overall energy metabolism during reperfusion of the working heart after inducement of ischemia as set forth in claim 43,
      wherein a change in the overall endogenous and exogenous fatty acid utilization, the overall measure of glucose metabolism, the complete energy metabolism, the exogenous energy metabolism, the overall energy metabolism of the heart during ischemia, or, the overall energy metabolism during reperfusion of the working heart after inducement of ischemia, after addition of the test compound indicates that the test compound can modulate the energy metabolism of a working heart.

45. A method for screening for compounds capable of modulating the energy metabolism of a working heart comprising the following steps
   (a) providing an isolated working heart;
   (b) contacting the isolated working heart with a test compound;
   (c) measuring the overall endogenous and exogenous fatty acid utilization of the heart as set forth in claim 1, the overall measure of glucose metabolism of the heart as set forth in claim 18, the complete energy metabolism of the heart as set forth in claim 30, the exogenous energy metabolism of the heart as set forth in claim 36, the overall energy metabolism of the heart during ischemia as set forth in claim 42, or, the overall energy metabolism during reperfusion of the working heart after inducement of ischemia as set forth in claim 43;
   (d) contacting the isolated working heart without or with more or less of the test compound; and
   (e) measuring the change in overall fatty acid utilization of the heart as set forth in claim 1, the overall measure of glucose metabolism of the heart as set forth in claim 18, the complete energy metabolism of the heart as set forth in claim 30, the exogenous energy metabolism of the heart as set forth in claim 36, the overall energy metabolism of the heart during ischemia as set forth in claim 42, or, the overall energy metabolism during reperfusion of the working heart after inducement of ischemia as set forth in claim 43,
      wherein a change in the overall endogenous and exogenous fatty acid utilization, the overall measure of glucose metabolism, the complete energy metabolism, the exogenous energy metabolism, the overall energy metabolism of the heart during ischemia, or, the overall energy metabolism during reperfusion of the working heart after inducement of ischemia, after withdrawal or dilution or increase in amount of the test compound indicates that the test compound can modulate the energy metabolism of a working heart.

46. The method of claim 44 or claim 45, wherein the isolated working heart is a mammalian heart.

47. The method of claim 46, wherein the isolated working heart is a rabbit heart, a rat heart or a mouse heart.

48. The method of claim 44 or claim 45, wherein the test compound is administered to the heart by perfusion.

49. A method for measuring complete energy metabolism in a working heart comprising the following steps
   (a) providing an isolated working heart;
   (b) measuring fatty acid oxidation and lactate oxidation in the working heart simultaneously; and
   (c) measuring glycolysis, glucose oxidation, triacylglycerol turnover and glycogen turnover in the working heart, wherein the glycolysis, glucose oxidation, triacylglycerol turnover and glycogen turnover are measured simultaneously, or, serially, wherein step (c) can be performed after step (b), thereby measuring complete energy metabolism in the working heart.

50. A method for measuring overall energy metabolism in an ischemic working heart comprising the following steps (a) providing an isolated ischemic working heart, wherein the ischemia is induced by perfusion at a low flow rate;

(b) measuring fatty acid oxidation and lactate oxidation in the ischemic working heart simultaneously; and (c) measuring glycolysis, glucose oxidation, triacylglycerol turnover and glycogen turnover in the ischemic working heart, wherein the glycolysis, glucose oxidation, triacylglycerol turnover and glycogen are measured simultaneously, or, serially, wherein step (c) can be performed after step (b), thereby measuring overall energy metabolism in the ischemic working heart.

51. A method for measuring overall energy metabolism during reperfusion in an ischemic working heart comprising the following steps (a) providing an isolated reperfused working heart, wherein the reperfusion begins after ischemia is induced in the heart;

(b) measuring fatty acid oxidation and lactate oxidation in the reperfused working heart simultaneously; followed by (c) measuring glycolysis, glucose oxidation, triacylglycerol turnover and glycogen turnover in the reperfused working heart, wherein the glycolysis, glucose oxidation, triacylglycerol turnover and glycogen are measured serially, thereby measuring overall energy metabolism during reperfusion of the ischemic working heart.

* * * * *